United States Patent [19]

Rinehart

[11] 4,075,006

[45] Feb. 21, 1978

[54] S-ARYL N-ALKYNYLTHIOLCARBAMATES

[75] Inventor: Jay K. Rinehart, Akron, Ohio

[73] Assignee: PPG Industries, Inc., Pittsburgh, Pa.

[21] Appl. No.: 710,057

[22] Filed: July 30, 1976

[51] Int. Cl.$^2$ .................. A01N 9/12; C07C 155/08
[52] U.S. Cl. .................................. 71/100; 260/455 A
[58] Field of Search ................. 260/455 A; 71/100

[56] References Cited

U.S. PATENT DOCUMENTS

| | | | |
|---|---|---|---|
| 3,301,885 | 1/1967 | Richter et al. | 71/100 |
| 3,687,997 | 8/1972 | Kiehs et al. | 260/455 A |

Primary Examiner—Delbert R. Phillips
Attorney, Agent, or Firm—Robert J. Grassi

[57] ABSTRACT

Novel S-aryl N-alkynylthiolcarbamates such as S-4-methoxyphenyl N-(1,1-dimethyl-2-propynyl)thiolcarbamate which are useful for controlling the effect on plants of plant pests such as pathogenic nematodes, fungi, or other pathogenic organisms; particularly Meloidogyne nematodes, *Sclerotium rolfsii, Fusarium solani*, and *Puccinia rubigo-vera* are disclosed. The methods of controlling plant pests with these thiolcarbamates are also disclosed.

18 Claims, No Drawings

S-ARYL N-ALKYNYLTHIOLCARBAMATES

BACKGROUND OF THE INVENTION

This invention concerns novel S-aryl N-alkynylthiolcarbamates, particularly those in which the alkynyl has from three to five carbon atoms. This invention also concerns methods of controlling the effect on plants of plant pests, particularly Meliodogyne nemas, *Fusarium solani, Sclerotium rolfsii,* and *Puccinia rubigo-vera.*

DESCRIPTION OF THE PRIOR ART

Plant pests such as weeds, nematodes, fungi, bacteria, insects, virus and other microorganisms continually affect the growth of crops, trees, and other desirable vegetation. One method of controlling plant pests is by application of chemicals which affect the plant pests. These chemicals are applied to the soil, to the desirable plant, or directly to the plant pest itself. Because millions of plant pests exist and differ in tolerance to chemicals, new chemicals must be discovered which are effective to control the deleterious effects of plant pests. The prior art, shows that certain thiolcarbamates are active against certain plant pests. The following patents and references illustrate thiolcarbamates claimed to be effective against certain plant pests.

U.S. Pat. Nos. 2,977,209 and 3,265,563 disclose S-phenyl N-alkylthiolcarbamates, S-chlorophenyl N-alkylthiolcarbamates, S-ethoxyphenyl N-allylcarbamates, S-chlorophenyl N-alkylthiolcarbamates, S-ethoxyphenyl N-alkylthiolcarbamates, S-p-tolyl N-alkylthiolcarbamates, and S-2,4-dimethylphenyl N-alkylthiolcarbamates as herbicides and fungicides. U.S. Pat. No. 3,632,332 discloses S-4-methylbenzyl N,N-diethylthiocarbamate as a herbicide for rice fields. U.S. Pat. No. 3,301,885 discloses S-substituted phenyl N-alkyl, N-alkoxythiolcarbamates as herbicides, miticides, and insecticides. U.S. Pat. No. 3,687,653 discloses trifluoromethylbenzyl N-alkylthiolcarbamates as herbicides. U.S. Pat. No. 3,046,189 and Canadian Pat. No. 789,575 disclose S-alkyl N-alkylthiocarbamates as nematocides. R. Reimschneider and O. Lorenz, in *Monstsch.*, 84, 518 (1953) described S-phenyl N,N-dimethylthiolcarbamate, and D. G. Crosby and C. Niemann, *Journal of American Chemical Society,* 76, 4458 (1954) describe S-phenyl N-cyclohexylthiolcarbamate, and S-phenyl N-phenylthiolcarbamate. Netherlands Pat. No. 6,606,753 discloses S-phenyl N-trifluoromethylphenylthiocarbamate and S-substituted phenyl N-substituted trifluoromethylphenylthiocarbamates as anthelmintics. M.S. Newman and H. A. Karnes, *Journal of Organic Chemistry,* 31, 3980–3983 (1966) described S-β-naphthyl N,N-dimethylthiolcarbamate, S-2-nitrophenyl N,N-dimethylthiolcarbamate, S-3-nitrophenyl N,N-dimethylthiolcarbamate, S-2,4,5-trichlorophenyl N,N-dimethylthiolcarbamate, S-3-trifluoromethylphenyl N,N-dimethylthiolcarbamate, S-2,3,5,6-tetramethylphenyl N,N-dimethylthiolcarbamate, S-4-tert-butylphenyl N,N-dimethylthiolcarbamate, S-2-methoxyphenyl N,N-dimethylthiolcarbamate, and S-4-methoxyphenyl N,N-dimethylthiolcarbamate.

U.S. Pat. No. 3,932,632 discloses insecticides of dithiophosphate compounds mixed with S-aryl N,N-alkylthiolcarbamates, or S-aryl N,N-alkylenethiolcarbamates, or S-aryl N,N-alkynylthiocarbamates, or S-aryl N,N-(alkyl, alkylene, or alkynyl) (alkyl, alkylene, or alkynyl)thiolcarbamates where the aryl may be a substituted phenyl.

SUMMARY OF THE INVENTION

This invention concerns novel agriculturally useful S-aryl N-alkynylthiolcarbamates represented by the general graphic formula:

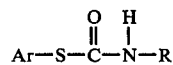

wherein:

Ar is an aryl of phenyl, 4-chlorophenyl, 4-bromophenyl, 4-fluorophenyl, 3,4-dichlorophenyl, 4-nitrophenyl, 3-alkoxyphenyl in which the alkoxy has from one to four carbon atoms, 4-alkoxyphenyl in which the alkoxy has from one to four carbon atoms, 3-alkylphenyl in which the alkyl has from one to four carbon atoms, and 4-alkylphenyl in which the alkyl has from one to four carbon atoms, and R is an alkynyl of 2-propynyl, 2-butynyl, 3-butynyl, 2-pentynyl, 3-pentynyl, 4-pentynyl, 1-methylprop-2-ynyl, 1-ethylprop-2-ynyl, 1-methylbut-2-ynyl, and 1,1-dimethylprop-2-ynyl.

These compounds are used in controlling the deleterious effect of plant pests, such as *Meloidogyne nemas, Sclerotium rolfsii, Fusarium solani,* and *Puccinia rubigovera* on plants.

DESCRIPTION OF THE PREFERRED EMBODIMENTS

The novel compositions of N-alkynylthiolcarbamates, of this invention are represented by the following graphite formula:

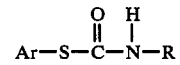

wherein:

Ar is an aryl.

The term "aryl" as used herein and in the claims refers to: phenyl, 4-chlorophenyl, 4-bromophenyl, 4-fluorophenyl, 3,4-dichlorophenyl, 4-nitrophenyl, 3-alkoxyphenyl in which the alkoxy has from one to four carbon atoms, 4-alkoxyphenyl in which the alkoxy has from one to four carbon atoms, 3-alkylphenyl in which the alkyl has from one to four carbon atoms, 4-alkylphenyl in which the alkyl has from one to four carbon atoms, and R is an alkynyl selected from the group consisting of 2-propynyl (—CH$_2$—C≡CH), 2-butynyl (CH$_2$—C≡C—CH$_3$), 2pentynyl (—CH$_2$—C≡C—CH$_2$—CH$_3$), 3-butynyl (—CH$_2$CH$_2$C≡CH), 4-pentynyl (—CH$_2$CH$_2$CH$_2$C≡CH), 3-pentynyl (—CH$_2$CH$_2$C≡C—CH$_3$), 1-methylprop-2-ynyl (—CH(CH$_3$)—C≡CH), 1-ethylprop-2-ynyl (—C(C$_2$H$_5$)—C≡CH), 1-methylbut-2-ynyl (—C(CH$_3$)—C≡C—CH$_3$), and 1,1-dimethylprop-2-ynyl (—C(CH$_3$)(CH$_3$)—C≡CH).

The phrase "3-alkoxyphenyl in which the alkoxy has from one to four carbon atoms" as used herein and in the claims, refers to:

3-methoxyphenyl, 3-ethoxyphenyl, 3-propoxyphenyl, 3-isopropoxyphenyl, 3-n-butoxyphenyl, 3-sec-butoxyphenyl, 3-isobutoxyphenyl, and 3-tert-butoxyphenyl.

The phrase "4-alkoxyphenyl in which the alkoxy has from one to four carbon atoms" as used herein and in the claims, refers to:

4-methoxyphenyl, 4-ethoxyphenl, 4-propoxyphenyl, 4-isopropoxyphenyl, 4-n-butoxyphenyl, 4-sec-butoxyphenyl, 4-isobutoxyphenyl, and 4-tert-butoxyphenyl.

The phrase "3-alkylphenyl in which the alkyl has from one to four carbon atoms" as used herein and in the claims, refers to:

3-methylphenyl, 3-ethylphenyl, 3-n-propylphenyl, 3-isopropylphenyl, 3-n-butylphenyl, 3-sec-butylphenyl, 3-isobutylphenyl, and 3-tert-butylphenyl.

The phrase "4-alkylphenyl in which the alkyl has from one to four carbon atoms" as used herein and in the claims, refers to:

4-methylphenyl, 4-ethylphenyl, 4-n-propylphenyl, 4-isopropylphenyl, 4-n-butylphenyl, 4-sec-butylphenyl, 4-isobutylphenyl, and 4-tert-butylphenyl.

Representative examples of those N-alkynylthiolcarbamates in which Ar is an aryl mentioned herein are, and R is an alkynyl mentioned herein:

S-phenyl N-1,1-dimethylprop-2-ynylthiolcarbarbamate;
S-4-chlorophenyl N-2-propynylthiolcarbamate;
S-4-fluorophenyl N-2-butynylthiolcarbamate;
S-4-bromophenyl N-2-pentynylthiolcarbamate;
S-3,4-dichlorophenyl N-3-butynylthiolcarbamate;
S-4-nitrophenyl N-3-pentynylthiolcarbamate;
S-3-methoxyphenyl N-4-pentynylthiolcarbamate;
S-3-ethoxyphenyl N-1-methylprop-2-ynylthiolcarbamate;
S-3-propoxyphenyl N-1-ethylprop-2-ynylthiolcarbamate;
S-3-isopropoxyphenyl N-1-methylbut-2-ynylthiolcarbamate;
S-3-n-butoxyphenyl N-1,1-dimethylprop-2-ynylthiolcarbamate;
S-3-sec-butoxyphenyl N-2-propynylthiolcarbamate;
S-3-isobutoxyphenyl N-4-pentynylthiolcarbamate;
S-3-tert-butoxyphenyl N-2-butynylthiolcarbamate;
S-4-methoxyphenyl N-2-pentynylthiolcarbamate;
S-4-ethoxyphenyl N-2-propynylthiolcarbamate;
S-4-propoxyphenyl N-3-butynynlthiolcarbamate;
S-4-isopropoxyphenyl N-3-pentynylthiolcarbamate;
S-4-n-butoxyphenyl N-4-pentynylthiolcarbamate;
S-4-isobutoxyphenyl N-1-methylprop-2-ynylthiolcarbamate;
S-4-sec-butoxyphenyl N-1-ethylprop-2-ynylthiolcarbamate;
S-4-tert-butoxyphenyl N-1-methylbut-2-ynylthiolcarbamate;
S-3-methylphenyl N-2-propynylthiolcarbamate;
S-3-ethylphenyl N-2-butynylthiolcarbamate;
S-3-n-propylphenyl N-3-butynylthiolcarbamate;
S-3-isopropylphenyl N-2-pentynylthiolcarbamate;
S-3n-butylphenyl N-3-pentynylthiolcarbamate;
S-3-isobutylphenyl N-4-pentynylthiolcarbamate;
S-3-sec-butylphenyl N-1-methylprop-2-ynylthiolcarbamate;
S-3-tert-butylphenyl N-1-ethylprop-2-ynylthiolcarbamate;
S-4-methylphenyl N-2-propynylthiolcarbamate;
S-4-ethylphenyl N-2-butynylthiolcarbamate;
S-4-n- propylphenyl N-3-butynylthiolcarbamate;
S-4-isopropylphenyl N-2-pentynylthiolcarbamate;
S-4n-butylphenyl N-3-pentynylthiolcarbamate;
S-4-isobutylphenyl N-4-pentynylthiolcarbamate;
S-4-sec-butylphenyl N-1,1-dimethyl-2-propynylthiolcarbamate; and
S-4-tert-butylphenyl N-1-methylbut-2-ynylthiolcarbamate.

The S-aryl N-alkynylthiolcarbamates in which R is 2-propynyl, 1-methylprop-2-ynyl, or 1,1-dimethylprop-2-ynyl are preferred. Representative examples of which are:

S-phenyl N-2-propynylthiolcarbamate;
S-4-chlorophenyl N-1-methylprop-2-ynylthiolcarbamate;
S-4-fluorophenyl N-1,1-dimethylprop-2-ynylthiolcarbamate;
S-4-bromophenyl N-2-propynylthiolcarbamate;
S-3,4-dichlorophenyl N-2-propynylthiolcarbamate;
S-4-nitrophenyl N-1-methylprop-1-ynylthiolcarbamate;
S-3-methoxyphenyl N-1,1-dimethylprop-2-ynylthiolcarbamate;
S-3-ethoxyphenyl N-2-propynylthiolcarbamate;
S-3-propoxyphenyl N-1-methylprop-2-ynylthiolcarbamate;
S-3-isopropoxyphenyl N-1,1-dimethylprop-2-ynylthiolcarbamate;
S-3-n-butoxyphenyl N-1-methylprop-2-ynylthiolcarbamate;
S-3-sec-butoxyphenyl N-1,1-dimethylprop-2-ynylthiolcarbamate;
S-3-isobutoxyphenyl N-1,1-dimethylprop-2-ynylthiolcarbamate;
S-3-tert-butoxyphenyl N-2-propynylthiolcarbamate;
S-4-methoxyphenyl N-1,1-dimethylprop-2-ynylthiolcarbamate;
S-4-ethoxyphenyl N-2-propynylthiolcarbamate;
S-4-propoxyphenyl N-1-methylprop-2-ynylthiolcarbamate;
S-4-isopropoxyphenyl N-1,1-dimethylprop-2-ynylthiolcarbamate;
S-4-n-butoxyphenyl N-1-methylprop-2-ynylthiolcarbamate;
S-4-isobutoxyphenyl N-1-methylprop-2-ynylthiolcarbamate;
S-4-sec-butoxyphenyl N-1,1-dimethylprop-2-ynylthiolcarbamate;
S-4-tert-butoxyphenyl N-2-propynylthiolcarbamate;
S-3-methylphenyl N-1,1-dimethylprop-2-ynylthiolcarbamate;
S-3-ethylphenyl N-2-propynylthiolcarbamate;
S-3-n-propylphenyl N-1-methylprop-2-ynylthiolcarbamate;
S-3-isopropylphenyl N-1,1-dimethylprop-2-ynylthiolcarbamate;
S-3-n-butylphenyl N-1-methylprop-2-ynylthiolcarbamate;
S-3-isobutylphenyl N-1-methylprop-2-ynylthiolcarbamate;

S-3-sec-butylphenyl N-1,1-dimethylprop-2-ynylthiolcarbamate;
S-3-tert-butylphenyl N-2-propynylthiolcarbamate;
S-4-methylphenyl N-1,1-dimethylprop-2-ynylthiolcarbamate;
S-4-ethylphenyl N-2-propynylthiolcarbamate;
S-4-n-propylphenyl N-1-methylprop-2-ynylthiolcarbamate;
S-4-isopropylphenyl N-1,1-dimethylprop-2-ynylthiolcarbamate;
S-4-n-butylphenyl N-1-methylprop-2-ynylthiolcarbamate;
S-4-isobutylphenyl N-1-methylprop-2-ynylthiolcarbamate;
S-4-sec-butylphenyl N-1,1-dimethylprop-2-ynylthiolcarbamate; and
S-4-tert-butylphenyl N-2-propynylthiolcarbamate.

Those S-aryl N-alkynylthiolcarbamates in which R is 1,1-dimethyl-2-propynyl are especially preferred, such as:

S-phenyl N-1,1-dimethylprop-2-ynylthiolcarbamate;
S-4-chlorophenyl N-1,1-dimethylprop-2-ynylthiolcarbamate;
S-4-fluorophenyl N-1,1-dimethylprop-2-ynylthiolcarbamate;
S-4-bromophenyl N-1,1-dimethylprop-2-ynylthiolcarbamate;
S-3,4-dichlorophenyl N-1,1-dimethylprop-2-ynylthiolcarbamate;
S-4-nitrophenyl N-1,1-dimethylprop-2-ynylthiolcarbamate;
S-3-methoxyphenyl N-1,1-dimethylprop-2-ynylthiolcarbamate;
S-3-ethoxyphenyl N-1,1-dimethylprop-2-ynylthiolcarbamate;
S-3-propoxyphenyl N-1,1-dimethylprop-2-ynylthiolcarbamate;
S-3-isopropoxyphenyl N-1,1-dimethylprop-2-ynylthiolcarbamate;
S-3-n-butoxyphenyl N-1,1-dimethylprop-2-ynylthiolcarbamate;
S-3-sec-butoxyphenyl N-1,1-dimethylprop-2-ynylthiolcarbamate;
S-3-isobutoxyphenyl N-1,1-dimethylprop-2-ynylthiolcarbamate;
S-3-tert-butoxyphenyl N-1,1-dimethylprop-2-ynylthiolcarbamate;
S-4-methoxyphenyl N-1,1-dimethylprop-2-ynylthiolcarbamate;
S-4-ethoxyphenyl N-1,1-dimethylprop-2-ynylthiolcarbamate;
S-4-propoxyphenyl N-1,1-dimethylprop-2-ynylthiolcarbamate;
S-4-isopropoxyphenyl N-1,1-dimethylprop-2-ynylthiolcarbamate;
S-4-n-butoxyphenyl N-1,1-dimethylprop-2-ynylthiolcarbamate;
S-4-isobutoxyphenyl N-1,1-dimethylprop-2-ynylthiolcarbamate;
S-4-sec-butoxyphenyl N-1,1-dimethylprop-2-ynylthiolcarbamate;
S-4-tert-butoxyphenyl N-1,1-dimethylprop-2-ynylthiolcarbamate;
S-3-methylphenyl N-1,1-dimethylprop-2-ynylthiolcarbamate;
S-3-ethylphenyl N-1,1-dimethylprop-2-ynylthiolcarbamate;
S-3-n-propylphenyl N-1,1-dimethylprop-2-ynylthiolcarbamate;
S-3-isopropylphenyl N-1,1-dimethylprop-2-ynylthiolcarbamate;
S-3-n-butylphenyl N-1,1-dimethylprop-2-ynylthiolcarbamate;
S-3-isobutylphenyl N-1,1-dimethylprop-2-ynylthiolcarbamate;
S-3-sec-butylphenyl N-1,1-dimethylprop-2-ynylthiolcarbamate;
S-3-tert-butylphenyl N-1,1-dimethylprop-2-ynylthiolcarbamate;
S-4-methylphenyl N-1,1-dimethylprop-2-ynylthiolcarbamate;
S-4-ethylphenyl N-1,1-dimethylprop-2-ynylthiolcarbamate;
S-4-n-propylphenyl N-1,1-dimethylprop-2-ynylthiolcarbamate;
S-4-isopropylphenyl N-1,1-dimethylprop-2-ynylthiolcarbamate;
S-4-n-butylphenyl N-1,1-dimethylprop-2-ynylthiolcarbamate;
S-4-isobutylphenyl N-1,1-dimethylprop-2-ynylthiolcarbamate;
S-4-sec-butylphenyl N-1,1-dimethylprop-2-ynylthiolcarbamate; and
S-4-tert-butylphenyl N-1,1-dimethylprop-2-ynylthiolcarbamate.

Those S-aryl N-alkynylthiolcarbamates mentioned herein in which the aryl is 4-methoxyphenyl, 3-methoxyphenyl, 3,4-dichlorophenyl, 4-chlorophenyl and phenyl are highly preferred, and of these highly preferred compounds those in which R is 2-propynyl, 1-methylprop-2-ynyl or 1,1-dimethylprop-2-ynyl are especially preferred. Specific examples being:

S-4-methoxyphenyl N-2-propynylthiolcarbamate;
S-4-methoxyphenyl N-1-methylprop-2-ynylthiolcarbamate;
S-4-methoxyphenyl N-1,1-dimethylprop-2-ynylthiolcarbamate;
S-3-methoxyphenyl N-2-propynylthiolcarbamate;
S-3-methoxyphenyl N-1-methylprop-2-ynylthiolcarbamate;
S-3-methoxyphenyl N-1,1-dimethylprop-2-ynylthiolcarbamate;
S-3,4-dichlorophenyl N-2-propynylthiolcarbamate;
S-3,4-dichlorophenyl N-1-methylprop-2-ynylthiolcarbamate;
S-3,4-dichlorophenyl N-1,1-dimethylprop-2-ynylthiolcarbamate;
S-4-chlorophenyl N-2-propynylthiolcarbamate;
S-4-chlorophenyl N-1-methylprop-2-ynylthiolcarbamate;
S-4-chlorophenyl N-1,1-dimethylprop-2-ynylthiolcarbamate;
S-phenyl N-2-propynylthiolcarbamate;
S-phenyl N-1-methylprop-2-ynylthiolcarbamate; and
S-phenyl N-1,1-dimethylprop-2-ynylthiolcarbamate.

The following compounds are particularly preferred:

S-4-methoxyphenyl N-1,1-dimethylprop-2-ynylthiolcarbamate;
S-3-methoxyphenyl N-1,1-dimethylprop-2-ynylthiolcarbamate;
S-3,4-dichlorophenyl N-1,1-dimethylprop-2-ynylthiolcarbamate;

S-4-chlorophenyl N-1,1-dimethylprop-2-ynylthiolcarbamate; and

S-phenyl N-1,1-dimethylprop-2-ynylthiolcarbamate.

SYNTHESIS OF THE COMPOUNDS

The following Example illustrates the synthesis of the S-aryl N-alkynylthiolcarbamates by the reaction of an arylthiochloroformate, having an aryl mentioned herein, with a primary amine having an alkynyl mentioned herein.

EXAMPLE I

S-4-methoxyphenyl N-(2,2-dimethyl-2-propynyl)thiolcarbamate

The synthesis route uses the rection of 4-methoxyphenylthiolchloroformate with 3-amino-3-methyl-1-butyne, which was prepared from 3-methyl-2-butyn-3-ol.

a. Synthesis of 4-Methoxyphenylthiolchloroformate

A one liter three-necked, creased (Morton) flash was equipped with a mechanical stirrer, dry ice condenser, thermometer, and phosgene inlet. The flask was charged with 4-methoxybenzenethiol (4-methoxyphenylthiol), (43.3 grams, 0.308 moles) and methylene chloride (250 millimeters). Phosgene gas (47 grams, 0.47 moles) was condensed over a 45 minute period, at about 1° Centigrade, into the stirred solution of methylene chloride and 4-methoxyphenylthiol. Then an aqueous solution (100 ml.) of sodium hydroxide (23.6 grams, 0.59 mole) was added dropwise into the stirred solution, at 3° to 8° Centigrade over a 40 minute period. Stirring was continued for one hour. The ice bath was removed and the dry ice condenser was replaced with a water cooled condenser. The reaction mixture was stirred for two hours at ambient temperature, and then degassed with a gentle stream of nitrogen at 35°-40° Centigrade for one and a half (1½) hours, at which time no phosgene was detected by a phosgene indicator solution (Nitroso reagent).

The organic and water phases were separated. The organic layer was dried with sodium sulfate ($Na_2SO_4$), and filtered, and the organic solvent was removed with a rotary evaporator leaving a pale yellow liquid (57.7 grams, 92.6 percent yield). This was purified by vacuum distillation through a 6 inch Vigreux column. The distillate of 4-methoxyphenylthiolchloroformate was a colorless liquid (43.8 grams, 70.3 percent yield); it had a boiling point of 78° to 80° Centigrade at 0.1 millimeter of mercury pressure. It had an infrared spectra with a carbonyl band (C=O) at 1760 reciprocal centimeters ($cm^{-1}$).

Analysis Calculated For: $C_8H_7ClO_2S$: C, 47.41 and H, 3.48 Found: C, 47.42, 47.24 and H, 3.36, 3.28 b. Synthesis of 3-Amino-3-methyl-1-butyne

3-Amino-3-methyl-1-butyne was synthesized by reacting 3-chloro-3-methyl-1-butyne with sodium amide in liquid ammonia. The 3-chloro-3-methyl-1-butyne was synthesized according to the method of G. F. Hennion and E. G. Teach, "The Preparation of Some Acetylenic Primary Amines", *Journal of the American Chemical Society*, Vol. 75, pages 1653–1654, (1953), using sodium amide which was prepared in situ by the method of Vaughn, Vogt, and Nieuwland, "A Rapid Catalytic Preparation of Sodamide in Liquid Ammonia and Some of its Uses in the Preparation of Acetylenic Materials", *Journal of the American Chemical Society*, Vol. 56, page 2120, (1934).

c. Synthesis of S-4-methoxyphenyl N-(2,2-dimethyl-2-propynyl)thiolcarbamate

A 500 milliliter three-necked creased (Morton) flask was equipped with a mechanical stirrer, a reflux condenser, a thermometer, and a dropping funnel. A solution containing 100 milliliters of water, 100 milliliters of ethylether, 4.5 grams (45 millimoles) of triethylamine and 3.7 grams (45 millimoles) of the above mentioned 3-amino-3-methyl-1-butyne was added to the flask. A solution containing 9.1 grams of 4-methoxyphenylthiolchloroformate (mentioned herein) in 10 milliliters of ethylether was added dropwise over a 20 minute period to the vigorously stirred amine solution. During the addition, the temperature rose from 24° to 29° Centigrade. The reaction mixture was stirred at ambient temperature for an additional half hour. The layers of the solution were separated; the aqueous layer was washed once with 100 milliliters of ethylether, and this ethylether washing and the ethylether layer of the solution were combined and were washed with 100 milliliters of aqueous solutions of 10 weight percent of sodium hydroxide, and 10 weight percent hydrochloric acid, respectively, and then were dried with anhydrous sodium sulfate ($Na_2SO_4$). After filtering off the sodium sulfate, the ethylether solvent was removed by evaporation with a rotary evaporator which left 8.9 grams (79.5percent yield) of a white crystalline material. The crystalline material was recrystallized from benzene, and 4.0 grams of the white crystalline product of S-4-methoxyphenyl N-(2,2-dimethyl-2-propynyl)thiolcarbamate formed. The product had a melting point of 105.5° to 109.5° Centigrade. Its infrared spectra had a N—H band at 3295 reciprocal centimeters ($cm^{-1}$) and a C=O band at 1665 $cm^-$.

Analysis Calculated For: $C_{13}H_{15}NO_2S$: C, 62.62; H, 6.06; and N, 5.62 Found: C, 62.60, 62.48; H, 5.79, 5.74; and N, 5.39, 5.33 d. Snythesis of the Other Compounds Disclosed Herein

The other compounds disclosed herein may also be synthesized by the reaction of the arylthiochloroformates formed from phosgene and the thiolaryls having an aryl mentioned herein with amines having an alkynyl mentioned herein. Thus, in lieu of 4-methoxyphenylthiol in the synthesis of 4-methoxyphenylthiochloroformate, one can substitute the other aryls mentioned herein, and in lieu of 3-amino-3-methyl-1-butyne in the above mentioned synthesis reaction the other amines of 3-amino-1-propyne, 1-amino-2-butyne, 4-amino-1-butyne, 1-amino-2-pentyne, 5-amino-2-pentyne, 5-amino-1-pentyne, 3-amino-3-methyl-1-propyne, and 3-amino-3-ethyl-1-propyne may be used.

In this synthesis reaction of an arylthiochloroformate with the alkyne amine, other inert solvents which dissolve the reactants and products, are easily removed from the products and having a boiling point appropriate to the reaction temperatures may be used in lieu of ethylether and water; such as methylethylether, methylpropylether, benzene, tetrahydrofuran, and chloroform.

The reaction temperature for the reaction of the thiochloroformates and amines may vary from 15° to 50° Centigrade.

In lieu of triethylamine other tertiary amines may be used in the reaction of the thiochloroformates and amines, such as trimethyl amine, tripropyl amines, or trialkyl amines in which the alkyl has up to 5 carbon atoms, or other proton acceptors may be used such as pyridine, alkyl substituted pyridines, sodium hydroxide, and potassium hydroxide.

Removal of the solvents, and reactants or other impurities from the S-4-methoxyphenyl N-(2,2-dimethyl-prop-2-ynyl)thiolcarbamate or the other S-aryl N-alkynylthiolcarbamates mentioned herein is not necessary except in so far as they interfere with the intended use of the compounds; such as their use for control of nematodes. All conventional purification techniques, such as recrystallization from solvents, fractional crystallization, washing with one or more solvents, followed by evaporation of the solvents, or filtration from the solvents, or their equivalents may be used.

Alternatively, the alkynyl amines mentioned herein could be reacted with phosgene to form the corresponding alkynylcarbamoyl chlorides which are then reacted with the appropriate arylthiol mentioned herein. These reactions may be carried out in the inert solvents mentioned herein, containing a stoichiometric amount of the acid acceptor mentioned herein, at the temperature ranges mentioned herein, to form the thiolcarbamates mentioned herein.

PROPERTIES

The S-aryl N-alkynylthiolcarbamates of this invention possess one or more properties which make them useful for agricultural applications to control plant pests, or the deleterious effects of plant pests, or both plant pests and their deleterious effects. Such properties are: the ability to systemically control the harmful effects of nematodes, particularly, root knot nematodes; the ability to control pathogenic nematodes by direct contact or by incorporation of the compound into soil prior to or after infestation with nematodes; and the ability to control diseases caused by certain pathogenic fungi or other microorganisms.

These useful properties of the compounds are illustrated by the following laboratory or greenhouse tests.

NEMATODE CONTROL OF ROOT-KNOT NEMATODE

This test illustrates control of the deleterious effect of nematodes upon tomatoes growing in soil infested with the pathogenic nematode *Meloidogyne incognita*.

In this test procedure a stock acetone solution consisting of 99.75 weight percent of acetone, 0.20 percent sorbitan trioleate (SPAN 85 ®) and 0.05 percent sorbitan monooleate polyalkylene derivative (TWEEN 80 ®) was used. The test compound was dissolved in an aliquot of the stock solution, and deionized water was added to form the desired concentration for spraying. For example, 1200 mg. of a test compound was dissolved in 80 grams of the stock acetone solution, and this solution was diluted to 100 grams, to form a spray solution containing 1200 ppm of the test compound.

Bonny Best tomato plants were grown in sterile soil from seedlings in a glass greenhouse, which used natural sunlight, for four or five weeks until their height was 6 to 8 inches, and they had at least three fully expanded leaves (usually more).

The growing tomato plants were separated into two groups, one for spray treatment (treated) and the other to serve as the control. The plants being treated were passed through a spraying machine which sprays them with the previously prepared test solution. The control group was not sprayed.

The solution of the test compound was applied as a spray by passing a tray of pots containing tomato plants, under a sprayer equipped with a T-Jet 8001-E spray nozzle tip and operating in the range of 35–40 pounds per square inch of pressure. The pot containing the plant was loaded within a tray and placed on a conveyor belt moving at about 0.0625 mph (5.49 feet per minute). When the tray passed under the spray head, it tripped a micro-switch which operated the sprayer. The spray was applied to the dripping point. The spray rate was equivalent to 200 gallons per surface acre (lbs. ai/200 gal/acre). The sprayed plants were dried, then they and the control plants were transplanted in soil infested with the root-knot nematodes (*Meloidogyne incognita*), and grown under greenhouse conditions, using natural sunlight, at an average temperature of 60°–70° F. in the winter and 70°–80° F. in the summer.

Both the sprayed (treated) and control plants were uprooted four (4) weeks after being transplanted in infested soil, and their roots were examined for root-knots which were counted in accordance with the method of W. M. Zeck, *Pflanzenschutz - Nachrichten*, Vol. 24, pages 141–144 (1971). The control was also rated according to the Zeck Index. The root-knot counts were related to percent control by the following formula:

$$\text{Percent Control} = 100\% - \frac{\text{(number of root knots in treated plants)}}{\text{(number of root knots in control plants)}} (100\%)$$

Vydate (Dupont 1410 - methyl N',N'-dimethyl-N-[(methylcarbamoyl) oxy]-1-thioxamimidate) a systemic nematocide known to be effective against the root-knot nematodes was also tested at the same concentration as the test compoumd and under the same conditions, as an internal check. Treated plants were also observed for evidence of damage by the applied test compound.

Five replicates per concentration of the test compound were made. Each replicate's percentage was based on the average of the percent control obtained for 2 plants. An average percent control value of 10 or higher indicates that systemic control of the deleterious effects of nematodes on the test plants was achieved.

Test results obtained from these tests are shown in Table 1. Column 1 gives the example number of the test; column 2 gives the test compound used; column 3 gives the concentration (conc.) of test compound applied expressed as parts per million (ppm) as well as that of the check compound Vydate; column 4 gives the individual percent control per replicate (2 plants) for the test compound at the indicated concentration; column 5 gives individual percent control per replicate (2 plants) for the check compound Vydate at the indicated concentration; and column 6 gives the average Zeck Index rating of the control plants.

TABLE 1

CONTROL OF ROOT-KNOT NEMATODE, (*Meloidogyne incognita*) UPON TOMATO PLANTS

| Example No. | Compound (3) Applied | Conc. ppm. | Percent Control-Replicate | | | | | Check Compound-Vydate Percent Control-Replicate | | | | | Zeck Index Rating |
|---|---|---|---|---|---|---|---|---|---|---|---|---|---|
| | | | 1 | 2 | 3 | 4 | 5 | 1 | 2 | 3 | 4 | 5 | |
| II | S-phenyl N-methylthiol-carbamate (4) | 500 | 80 | 87 | 82 | 33 | 78 | 78 | 55 | 56 | 42 | 47 | a |
| III | " | 50 | 30 | 33 | 73 | 78 | 91 | 55 | 42 | 0 | 0 | 55 | b |
| IV | " | 5 | 55 | 73 | 33 | 82 | 67 | 0 | 36 | 24 | 0 | 0 | c |
| V (2) | S-phenyl N-methylthiol-carbamate (4) | 500 | 72 | 58 | 44 | 44 | 15 | 44 | 44 | 72 | 72 | 86 | 7.1 |
| VI (2) | S-phenyl N-methylthiol-carbamate (4) | 50 | 30 | 44 | 58 | 44 | 30 | 44 | 15 | 44 | 44 | 15 | 7.1 |
| VII (2) | " | 5 | 44 | 44 | 30 | 30 | 30 | 15 | 15 | 0 | 0 | 0 | 7.1 |
| VIII | S-phenyl N-methylthiol-carbamate (4) | 4000 | 100 | 100 | 75 | 50 | 100 | 100 | 100 | 100 | 100 | 100 | 4.0 |
| IX | " | 2000 | 100 | 75 | 75 | 75 | 75 | 100 | 100 | 100 | 100 | 75 | 4.0 |
| X | " | 1000 | 50 | 100 | 75 | 75 | 75 | 100 | 100 | 75 | 75 | 75 | 4.0 |
| XI | " | 500 | 50 | 50 | 75 | 50 | 75 | 75 | 100 | 50 | 50 | 75 | 4.0 |
| XII (2) | S-phenyl N-methylthiol-carbamate (4) | 500 | 59 | 46 | 59 | 73 | 73 | 59 | 59 | 73 | 86 | 86 | 7.4 |
| XIII (2) | S-phenyl N-methylthiol-carbamate | 50 | 73 | 59 | 59 | 46 | 59 | 59 | 59 | 59 | 73 | 59 | 7.4 |
| XIV (2) | " | 5 | 82 | 46 | 59 | 59 | 73 | 46 | 59 | 59 | 59 | 46 | 7.4 |
| XV | S-phenyl N-methylthiol-carbamate (4) | 1200 | 79 | 79 | 79 | 58 | 79 | 79 | 79 | 79 | 58 | 79 | 4.8 |
| XVI | " | 600 | 79 | 79 | 58 | 79 | 58 | 79 | 79 | 58 | 79 | 58 | 4.8 |
| XVII | S-phenyl N-methylthiol-carbamate | 300 | 37 | 37 | 58 | 17 | 17 | 37 | 37 | 58 | 17 | 37 | 4.8 |
| XVIII | S-phenyl N-allylthiol-carbamate (5) | 500 | 46 | 32 | 32 | 32 | 32 | 59 | 59 | 73 | 86 | 86 | 7.4 |
| XIX | " | 50 | 46 | 46 | 19 | 19 | 19 | 59 | 59 | 59 | 73 | 59 | 7.4 |
| XX | " | 5 | 19 | 19 | 32 | 32 | 32 | 46 | 59 | 59 | 59 | 46 | 7.4 |
| XXI | S-4-chlorophenyl N-methyl-thiolcarbamate (4) | 500 | 62 | 55 | 77 | 85 | 52 | 77 | 47 | 75 | 62 | 62 | a |
| XXII | " | 50 | 0 | 100 | 100 | 85 | 37 | 32 | 27 | 75 | 62 | 70 | b |
| XXIII | " | 5 | 35 | 15 | 37 | 100 | 60 | 15 | 75 | 50 | 0 | 0 | c |
| XXIV | S-4-methoxyphenyl N-(2,2-dimethyl-2-propynyl) thiolcarbamate | 1000 | 100 | 100 | 75 | 100 | 25 | 100 | 100 | 75 | 75 | 75 | 4.0 |
| XXV | S-4-methoxyphenyl N-(2,2-dimethyl-2-propynyl) thiolcarbamate | 500 | 75 | 25 | 50 | 100 | 50 | 75 | 100 | 50 | 50 | 75 | 4.0 |
| XXVI | " | 500 | 44 | 44 | 58 | 58 | 72 | 59 | 59 | 73 | 86 | 86 | 4.0 |
| XXVII | " | 50 | 30 | 58 | 44 | 58 | 44 | 44 | 15 | 44 | 44 | 15 | 7.1 |
| XXVIII | " | 5 | 58 | 58 | 44 | 44 | 44 | 15 | 15 | 0 | 0 | 0 | 7.1 |

(1) This compound gave a trace burn which the plant outgrew. Herbicidal rating of 1B; all other compounds tested had no effect upon the plants at the concentration at which the compounds were tested.
(2) At high Zeck Index Rating only the root knots on outer roots of the plant which are near the soil surface and sides of the pot are counted at Zeck Index of 7.4 the average number of root knots on the outer roots of the control plants were 266 root knots.
(3) Unless otherwise indicated, the novel test compounds are those formed by the synthesis described herein. The known compounds were synthesized as described in the prior art.
(4) These compounds are described in U.S. Pat. No. 2,977,209 and U.S. Pat. No. 3,265,563 and claimed for use as a systemic nematocide in Applicant's copending application entitled SYSTEMIC NEMATOCIDES, Serial No. 408,775, filed October 23, 1973.
(5) Compounds described in U.S. Pat. No. 2,977,209 and U.S. Pat. No. 3,265,563.
a The average number of root knots for the untreated plants was 55 ± 6 knots (low Zeck Rating)
b The average number of root knots for the untreated plants was 53 ± 7 knots
c The average number of root knots for the untreated plants was 40 ± 13 knots

CONTROL OF ROOT-KNOT NEMATODE (*Meloidogyne incognita*) UPON TOMATO PLANTS

TEST PROCEDURE

The test compound (generally as a solution) was added to a sample of soil pasteurized at 220° F. for 20 minutes and thoroughly blended therein with a soil blender.

An equivalent weight of the pasteurized soil was thoroughly blended with soil infested with *Meloidogyne incognita*.

The blends of chemical treated soil and nematode infested soil were then thoroughly mixed together in a soil blender. The amount of chemical compound added is expressed as pounds per acre of 3 inch depth of soil calculated on the basis that the value of a 3 inch acre of soil is approximately one million pounds.

The chemically treated nematode infested soil was potted and seeded with Bonny Best tomato seeds and watered (treated samples).

A sample of infested soil which has not been chemically treated with the test compounds was also potted and seeded with Bonny Best tomato seeds and watered (control samples).

A sample of infested soil was chemically treated with a known nematocide, Nemagon (1,2-dichloro-3-bromopropane) potted and seeded with Bonny Best tomato seed and watered (internal check samples).

The treated, control, and internal samples were placed in a glass covered greenhouse, and grown under natural sunlight for about 18 days to allow for germination of the seeds and growth of the plants. The temperature and humidity of the greenhouse varied from 70° to 80° F. and 50 to 90 percent relative humidity. The plants were uprooted and the root knots were counted as described hereinbefore and percent control was calculated according to the following formula:

$$\text{Average Percent Control} = 100\% - \frac{\text{(number of root knots in treated plants)}}{\text{(number of root knots in control plants)}} (100\%)$$

The results of these tests are shown in Table 2. Column 1 of Table 2 lists the example number; column 2 lists the compound tested; column 3 gives the test results, at an application rate of 50 pounds per acre; and column 4 gives the percent control for Nemagon at 5 pounds per acre. Unless otherwise indicated, the compound had no herbicidal effect upon the test plant. In some examples, results are shown for repeated tests as well as at different application rates. The test compounds used were synthesized as described herein. A value greater than 10 percent indicates soil control of the deleterious effect of the nemas upon the plants.

in Sclerotium-inoculated soil with the actual count of infection loci on carrot slices in pasteurized soil.

Each test was based on a minimum of three replicates. The amount of test compound is expressed as pounds per acre (lb/A) for a 3 inch depth of soil.

Control effectiveness is expressed as percent control and was calculated by the following formula:

Percent Control =

TABLE 2
TEST RESULTS FOR SOIL CONTROL OF NEMATODES OF *Meloidogyne incognita*

| Example No. | Compound | Percent Control At 50 Pounds Per Acre | Percent Control For Nemagon At 5 Pounds Per Acre |
|---|---|---|---|
| XXIX | S-$\beta$-naphthyl N,N-dimethyl-thiolcarbamate[b] | 0 | 93[a] |
| XXX | S-phenyl N-methylthiolcarbamate[c] | 88 | 71 |
| XXXI | S-phenyl N-(1,1-dimethyl-2-propynyl)thiolcarbamate | 0 | 0 |
| XXXII | S-phenyl N,N-dimethylthiolcarbamate[c] | 0[d] | 98 |
| XXXIII | S-4-chlorophenyl N-methyl-thiolcarbamate[c] | 90 | 98 |
| XXXIV | S-4-chlorophenyl N,N-diallyl-thiolcarbamate[c] | 0 | 98 |
| XXXV | S-4-methoxyphenyl N-(1,1-dimethyl-2-propynyl)thiolcarbamate | 39 | 96[a] |

[a] percent control at 6 pounds per acre
[b] described in J. Organic Chemistry, 31, 3980–3983
[c] known compound disclosed in U.S. 2,977,209
[d] herbicidal effect on plants, rating 5:R, 5:B - moderate toxicity

SOIL FUNGICIDAL TESTS

EXAMPLES XXXVI to XLII

These fungicidal tests indicate if the test compound protects against the deleterious effects of one or more soil fungi *Sclerotium rolfsii* and *Fusarium solani*.

CONTROL OF *Sclerotium rolfsii*

TEST PROCEDURE

A blend of pasteurized soil (pasteurized at 220° F.) containing over winter stage sclerotia of *Sclerotium rolfsii* was made, and a blend of pasteurized soil and the test compound (normally added to the soil as a solution) was made. Then the chemically treated soil was mixed with an equivalent weight of the Sclerotium-inoculated soil, and the mixture placed in a blender and thoroughly blended to form a mixture containing 8 grams of sclerotia per 3000 milliliters of dry soil. The mixture was then equally divided, and each division was placed in a container, implanted with two carrot slices, water sealed, incubated for 4–5 days in a glass covered greenhouse, which operated at 70° to 80° F., a humidity range of 50 to 90 percent, with natural sunlight, and observed for infection growth. The final observation (treated samples) was made after the fifth day in the greenhouse. Containers of pasteurized soil only, pasteurized soil plus chemical, pasteurized soil plus Sclerotium inoculum (control) were also implanted with carrot slices, and incubated under the same conditions as the treated samples.

Control effectiveness of a test compound was determined by comparing the actual count of infection loci (visible to the naked eye) on carrot slices in soil chemically treated with the test compound, with the actual count of infection loci on carrot slices in Sclerotium-inoculated soil.

The severity of the disease was determined by comparing the actual count of infection loci on carrot slices $$100\% - \frac{\text{(number of infection loci in all treated carrots)}}{\text{(number of infection loci in all control carrots)}} \ 100\%$$

CONTROL OF *Fusarium solani*

TEST PROCEDURE

A blend of pasteurized soil containing spores of *Fusarium solani* and a blend of pasteurized soil containing the test compound (generally applied in the form of a solution) were made. The *Fusarium solani*-inoculated soil and chemically treated soil is thoroughly mixed in a soil blender to form a mixture containing $5 \times 10^6$ spores per 3000 milliliters of dry soil. After blending, the mixture was equally divided and each division was potted, implanted with seeds of California White Pea Bean, watered, placed in a greenhouse operating at a temperature range of 70°–80° F. and a humidity range of 50 to 95 percent, and observed for 21 days. The final observation was made on the 21st day.

Containers of pasteurized soil only, pasteurized soil plus test compound, pasteurized soil plus spores of Fusarium inoculum were also implanted with seeds of California White Pea Bean, watered and placed in the greenhouse (control plants).

Control effectiveness of the test compound was determined by comparing the final observation of the actual infested stem area (which was visible to the naked eye) of the plants in the chemically treated Fusarium-inoculated soil with the actual infected stem area of the plants in the Fusarium-inoculated soil.

The percent control was calculated from the data based on the following formula:

Percent Control =
$$100\% - \frac{\text{(infected stem area of plants in treated soil)}}{\text{(infected stem area of control plants)}} \ 100\%$$

Disease severity was determined by comparing the actual count of surviving plants from Fusarium-inoculated soil with the actual count of surviving plants from the pasteurized soil.

Each test consisted of at least three replicates.

In all the above-described tests the effect of the test compound upon the plants used in the test was also observed and reported.

The test results for the compounds as controls against soil fungi diseases are given in Table 3. In this Table, column 1 gives the example number, column 2 gives the test compound (unless otherwise indicated these were synthesized as described herein or according to the prior art), columns 3 and 4 give the percent control against the diseases caused by *Sclerotium rolfsii* (Sr) and *Fusarium solani* (Fs), when the compounds are applied at fifty (50) pounds per acre (lbs/A).

TABLE 3
TEST RESULTS FOR CONTROL
AGAINST THE SOIL FUNGI:
Sr - *Sclerotium rolfsii* and Fs - *Fusarium solani*

| | | Percent Control At 50 Pounds Per Acre | |
|---|---|---|---|
| Example | Compound | Sr | Fs |
| XXXVI | S-β-naphthyl N,N-dimethyl-thiolcarbamate[a] | 0 | 0[e] |
| XXXVII | S-phenyl N-methylthiol-carbamate[c] | 39 | 40[b] |
| XXXVIII | S-phenyl N-(1,1-dimethyl-2-propynyl)thiol-carbamate | 0 | 56[d] |
| XXXIX | S-4-chlorophenyl N-methyl-thiolcarbamate[c] | 57 | 54[e] |
| XL | S-4-chlorophenyl N-diallyl-thiolcarbamate[f] | 0 | 0 |
| XLI | S-phenyl N,N-dimethylthiol-carbamate[f] | 0 | 67[g] |
| XLII | S-4-methoxyphenyl N-(1,1-dimethyl-2-propynyl)thiolcarbamate | 47 | 61 |

[a]described in J. Organic Chemistry, 31, 3980–3983 (1966)
[b]effect at 25 pounds per acre
[c]known compound described and used in patents 2,977,209 and 3,265,563 and claims for use as a systemic nematode control in Applicant's copending application, SYSTEMIC NEMATOCIDE, Serial No. 408,775, filed October 23, 1973.
[d]herbicidal effect on the plant rating (slightly toxic)
[e]herbicidal effect on the plant rating (moderately toxic)
[f]known compound described in patent 2,977,209
[g]herbicidal effect on the plant, rating 10 (killed the plant)

LEAF RUST OF WHEAT — PROTECTANT TEST PROCEDURE

This disease is caused by the fungus *Puccinia secondita* (Var.) *tritici*. The test procedure determines protectant properties of a compound; that is, whether the compound prevents plants from the effects of the disease, if the plants are contacted with the compound prior to exposure to the causal fungus.

In this test, wheat plants, *Triticum vulgare* (Cheyenne variety), approximately 7 to 8 days old and 4 to 5 inches tall, grown under natural sunlight in a glass covered greenhouse, were mounted on a compound turntable and sprayed to incipient run off at 40 pounds pressure for 60 seconds, equivalent to 50 gallons per acre, using solid cone T-Jet 8001-E spray nozzle, with a solution containing a pre-determined amount of the test compounds. The pre-determined amount of test compound was dissolved in a stock solution, the volume of which is equivalent to 19 percent by vol. of the total spray volume using 90 percent by vol. distilled water. The stock solution is an acetone emulsion solution, having 1995 ml. acetone, 4 ml. SPAN 85 ® (sorbitan trioleate), and 1 ml. TWEEN 80 ® (sorbitan monooleate polyalkylene derivative).

After the treated plants had dried, (4–8 hours), they were inoculated by uniformly dusting with spores of the fungus *Puccinia secondita* (Var.) *tritici*, taken directly from diseased plants, and incubated from 12 to 24 hours in the dark at 70° F. and 95 percent or more relative humidity, which normally insures that the spores have a chance to infest the plants. The plants were returned to the glass covered greenhouse, and observed for signs of orange pustules visible to the naked eye (normal infection stage which generally occurs after 3 to 5 days). The greenhouse was kept at a temperature of 70° to 80° F. and at a humidity of from 50 to 90 percent.

The severity of the disease was determined by the actual count of the developed pustules on inoculated but otherwise untreated controls. The test results are expressed as Percent Control which is determined by the actual count of the number of developed pustules appearing on the respectively treated plants compared directly to equivalent developed pustules on inoculated but otherwise untreated controls. This Percent Control is calculated as follows:

$$\text{Percent Control} = [1.00 - \frac{\text{No. Pustules on All Treated Plants}}{\text{No. Pustules on All Untreated Plants}}] \times 100$$

The foliar fungicidal test results are given in Table 4. Column 1 of Table 4 gives the example number; column 2 lists the test compound, which is prepared according to the synthesis given herein or as described in the prior art; and column 3 gives the percent control obtained at 1000 parts per million (ppm) for Leaf Rust of Wheat.

In all tests, the effect of the test compound on the plants was noted. For some compounds test results are given for lower test concentrations.

TABLE 4

| Example | Compound Applied | Percent Control At Diseases Leaf Rust of Wheat |
|---|---|---|
| XLIII | S-β-naphthyl N,N-dimethyl-thiolcarbamate[a] | 0 |
| XLIV | S-phenyl N-methylthiol-carbamate[b] | 100[c] |
| XLV | S-phenyl N-(1,1-dimethyl-2-propynyl)thiol-carbamate | 0 |
| XLVI | S-4-chlorophenyl N-methyl-thiolcarbamate[b] | 99[d] |
| XLVII | S-4-chlorophenyl N,N-diallylthiolcarbamate | 82[f] |
| XLVIII | S-4-methoxyphenyl N-(1,1-dimethyl-2-propynyl) thiolcarbamate | 87  75[f] |
| XLIX | S-phenyl N,N-dimethylthiol-carbamate[e] | 0[f] |
| L | S-3,4-dichlorophenyl N-2,3-dibromopropylthiolcarbamate | 100  100[a]  100[b]  89[c] |

[a]described in J. Organic Chemistry, 31, 3980–3983 (1966)
[b]known compound described in U.S. 2,977,209 and U.S. 3,265,563 and claimed for use as a systemic nematode control in Applicant's copending application entitled SYSTEMIC NEMATOCIDE, Serial No. 408,775, filed October 23, 1973.
[c]herbicidal effect on the plant rating moderately toxic
[d]herbicidal effect on the plant rating slightly toxic
[e]described in U.S. 2,977,209
[f]test results at test concentration of 500 ppm

APPLICATION a. Control of the Deleterious Effects of Nematodes Upon Plants

The deleterious effects of other nematodes of the genus Meloidogyne may be controlled by the substituted aryl N-alkynylthiolcarbamates, particularly S-4-methoxyphenyl N-(1,1-dimethyl-2-propynyl)thiolcarbamate. The species *Meloidogyne arenaria* (Peanut Root-knot Nematode), *Meloidogyne hapla* (Northern Root-knot Nematode), and Citrus root Nematode are examples of other Meloidogyne species which may be controlled. Ditylonchus destructor (Potato Rot Nematode) is another nematode which may be controlled by this compound. The *Meloidogyne incognita* nematode in particular is systemically controlled by the compound, S-4-methoxyphenyl N-(1,1-dimethyl-2-propynyl)thiolcarbamate.

Other species of nematodes may be controlled by applications other than systemic foliage contact, for example, by applying the active compounds to the soil or by dipping the bulbs in solutions of the active compounds. Examples of other nematodes are:

| | |
|---|---|
| *Aphelenchoides* species | Bud and Leaf Nematodes |
| *Anguina tritici* | Wheat Nematode |
| *Anguina agrostis* | Grass Nematode |
| *Belonolaimus* species | Sting Nematodes |
| *Criconemoides* species | Ring Nematodes |
| *Ditylonchus dipsaci* | Stem and Bulb Nematode |
| *Ditylonchus angustus* | Rice Nematode |
| *Dolichodorus heterocephalus* | Awl Nematode |
| *Helicotylenchus* species | Spiral Nematodes |
| *Heterodera rostochiensis* | Golden Nematode |
| *Heterodera tabacum* | Tobacco Cyst Nematode |
| *Heterodera schachtii* | Sugar Beet Nematode |
| *Heterodera carotae* | Carrot Root Nematode |
| *Heterodera gottingiana* | Pea Root Nematode |
| *Heterodera glycines* | Soybean Cyst Nematode |
| *Hoplolaimus* species | Lance Nematodes |
| *Pratylenchus brachyurus* | Smooth-headed Lesion Nematode |
| *Pratylenchus* species | Meadow Nematodes |
| *Pratylenchus musicola* | Banana Nematode |
| *Pratylenchus zeae* | Corn Nematode |
| *Radopholus similis* | Burrowing Nematode |
| *Rotylenchus reniformis* | Kidney-shaped Nematode |
| *Trichodorus* species | Stubby-root Nematodes |
| *Tylenchorhynchus claytoni* | Tobacco Stunt Nematode |
| *Xiphinema* species | Dagger Nematodes | b. Use of Formulations to Control Plant Pests

Although plants may be contacted with S-4-methoxyphenyl N-(2,2-dimethyl-2-propynyl)thiolcarbamate itself and the other compounds disclosed herein in an amount effective to control the deleterious effects of the plant pest; it is, however, preferable to use suitable agricultural formulations which contain other ingredients which enhance application of the compound. These agricultural formulations will generally comprise from 5 percent to 95 percent by weight of S-4-methoxyphenyl N-(2,2-dimethyl-2-propynyl)thiolcarbamate, or of the other compounds disclosed herein, or mixtures of these compounds, and either from 1 percent to 95 percent by weight of an agricultural diluent, or from 1 percent to 20 percent by weight of a surface active agent and other ingredients required to produce wettable powders, dusts, solutions, emulsifiable concentrates, granules, and the like, or both.

Wettable powders will contain from 25 to 80 percent active ingredients, from 0.1 percent to 5.0 percent wetters and dispersants with the balance consisting of inorganic absorptive diluents.

Since some compounds are solids, others are liquids, and others are viscous materials, they may be dissolved in one or more solvents and then sprayed upon the absorptive diluents of attapulgite clay, synthetic fine silica, and synthetic calcium and sodium alumino-silicates, or other solid insecticides, or foliar fungicides mentioned herein and then the solvent or solvents are evaporated off.

Emulsifiable oils will contain from 20 percent to 97 percent active ingredient, from 3.0 to 10.0 percent of an emulsifying agent, and may also contain from 1 percent to 77 percent water-immiscible solvent such as xylene or alkylated naphthalene.

Granules will contain from 5 percent to 25 percent active ingredient, and may also contain from 1 percent to 20 percent of a surfactant extended upon a granular base such as vermiculite or granular attapulgite. Granules produced by extrusion or tumbling will contain like amounts of active ingredients and surfactant.

c. Use of the Compounds With Other Known Pesticides

For the control of a wider range of crop-pests and diseases it is sometimes desirable to combine S-4-methoxyphenyl N-(2,2-dimethyl-2-propynyl)thiolcarbamate or other compounds with from 0.05 to 4 parts by weight of insecticides and fungicides, etc., known to be effective against crop-pests and diseases in concentrated premix or during the application step for foliar applications. Examples of other pesticides are: granules containing stable metal azide-metal salt formulations disclosed in assignee's copending application entitled AZIDE-METAL SALT FORMULATIONS, Ser. No. 624,357, filed Oct. 21, 1975, or S-4-methoxyphenyl N-2,3-dibromopropylthiolcarbamate, disclosed in assignee's copending application Ser. No. 631,751 filed Nov. 13, 1975 or S-4-methoxyphenyl N,N-bis(2,3-dibromopropyl)thiolcarbamate disclosed in assignee's copending application Ser. No. 631,802 filed Nov. 13, 1975, Sevin (1-naphthyl-N-methylcarbamate), Chlorobenzilate (ethyl 4,4'-dichlorobenzilate), Guthion (O,O-diethyl-S-[4-oxo-1,2,3-benzotriazin-3(4H)-yl-methyl]phosphorodithioate), Disyston (O,O-diethyl-S-[2-(ethylsulfinyl) ethyl]phosphorodithioate), Maneb (manganous ethylene bisdithiocarbamate), Karathane (mixture of 2,4-dinitro-6-octylphenylcrotonate, 2,6-dinitro4-octylphenylcrotonate, nitrooctylphenols (principally dinitro), 4-(1-methylheptyl)2,6-dinitrophenylcrotonate, 4-(1-ethylhexyl)2,6-dinitrophenylcrotonate, 4-(1-propylpentyl)2,6-dinitrophenylcrotonate, 6-(1-methylheptyl)2,4-dinitrophenylcrotonate, 6-(1-ethylhexyl)2,4-dinitrophenylcrotonate, and 6-(1-propylpentyl)2,4-dinitrophenylcrotonate), Blasticidin (blasticidin-S-benzylaminobenzensulfonate), Benlate (methyl 1-(butylcarbamoyl)-2-benzimidazolecarbamate), or Plantvax (5,6-dihydro-2-methyl1,4-oxathiin-3-carboxanilide-4,4-dioxide).

In some instances it is also desirable to include special purpose additives which will inhibit corrosion, reduce foaming, reduce caking, or increase flocculation.

The S-aryl N-alkynylthiolcarbamates of the general formula, especially those with the preferred alkynyls mentioned hereinbefore, such as S-4-methoxyphenyl N-(2,2-dimethyl-2-propynyl)thiolcarbamate, when used to control the deleterious effects of nematodes upon plants and plant parts, are applied in an effective amount as a suitable agricultural formulation within the vicinity of the infested area where the deleterious effects of the nematodes are to be controlled.

d. Controlling the Deleterious Effects of the Plant Pests

The phrase "contacting the plant with an amount effective" as used herein and in the claims means any method of bringing the plant and the compound into contact so that the deleterious effect of plant pest is controlled. This can be by spraying, dusting, dipping the plant into solutions, broadcasting the compound on the soil and discing it in. The method of contacting the plant will depend upon which plant pest's deleterious effects are to be controlled.

The phrase "to control the deleterious effects of plant pests upon the plants" as used herein and in the claims means that the adverse effects of the plant pests such as nematodes, fungi, and other organisms upon the plants are reduced in intensity so that the disease or root knots of chemically treated plants is from 10 to 90 percent of those of untreated plants. As used herein and in the claims, the phrase "an amount effective to control the deleterious effect of plant pests" is that amount necessary to give the desired control. This control may be direct control or systemic control which results from one mechanism or combination of several mechanisms; such as (a) direct killing of the plant pest such as nematodes or fungus; (b) repelling of the plant pest; or (c) rapid healing of the plant attacked by the plant pest. In systemic control, such as for nematodes of *Meloidogyne incognita*, S-4-methoxyphenyl N-(1,1-dimethyl-2-propynyl)thiolcarbamate and the other preferred compounds exhibiting systemic nematode control are applied to the foliage of the plant which has its roots infested by root nematodes, rather than directly to the infested area, e.g., the plant roots itself. Systemic control may result from a single mechanism or from a combination of mechansims. It may result from a translocation of the compound, i.e., S-4-methoxyphenyl N-(1,1-dimethyl-2-propynyl)thiolcarbamate (or a metabolite thereof) from its application site (e.g., the foliage), or to the area deleteriously affected by the nematodes (e.g., the roots, or the center portion or the stem) where it controls the deleterious effect; by (a) killing the nematodes; (b) repelling the nematodes; or (c) by healing the plant; or from translocation into the plant enzyme system where it induces the enzyme system to produce chemicals which (a) kill the nematodes or (b) repel them, or (c) which promote rapid healing of the plant. Systemic control may also result from a translocation of such a compound (or a metabolite of it) from its application site (foliage) through the plant to outside of the area (the roots) deleteriously affected by nematodes where it provides a protective shield against the nematodes; such as a root coating which repels or kills nematodes feeding upon this area of the plant.

e. Effective Amount of the Compounds to Use For Controlling the Deleterious Effect of Nematodes The effective amount varies with the particular nematode involved, the application method used, e.g., systemic, soil incorporation, or dusting with a powder, the type of formulation utilized, the plant species to be protected, and local conditions such as temperature, humidity, moisture content of the soil, nature of the soil and the like. Since many factors are involved, different rates of application are selected for best results depending upon these specific conditions.

For systemic control, the compounds of the general formula, and the preferred compounds, such as S-4-methoxyphenyl N-(1,1-dimethyl-2-propynyl)thiolcarbamate and the other compounds having systemic nematode control are preferably applied as a spray to the foliage of plants, particularly plants growing in soil infested with root-knot nematodes of the Meloidogyne species, particularly *Meloidogyne incognita*.

For systemic control of Meloidogyne species, particularly *Meloidogyne incognita*, the effective amount of S-4-methoxyphenyl N-(1,1-dimethyl-2-propynyl)thiolcarbamate and other preferred compounds and compounds of the general formula exhibiting systemic nematode control is a solution containing from 5 ppm to the maximum amount of the component tolerated by the plants which may be as high as 50,000 ppm applied as a spray to the dripping point. In general it is from 5 ppm to 10,000 ppm, normally from 5 ppm to 5000 ppm, and preferably from 5 ppm to 500 ppm. Those compounds in which R is 2-propynyl, 1,1-dimethylprop-2-ynyl, or 1-methylprop-2-ynyl are used at the low rates, while those thiolcarbamates with an aryl of 4-methoxyphenyl, 3-methoxyphenyl, 3,4-dichlorophenyl, 4-chlorophenyl, and phenyl are also used at the lower rates, and those in which R is 1,1-dimethylprop-2-ynyl are used at the lowest rates and are most preferred for systemic control.

The same amounts of these compounds of the general formula, i.e., S-4-methoxyphenyl N-(1,1-dimethyl-2-propynyl)thiolcarbamates are applied when these compounds are used in combination with insecticides such as Sevin, Chlorobenzilate, Guthion, Disyston, or foliar fungicides such as Maneb, Karathane, Blasticidin, Benlate, or Plantvax. The amount of these other insecticides or fungicides will be in accordance with the label instructions disclosed in technical literature given with these known commercial compounds. In some cases, better control of the deleterious effects of nematodes is obtained when the compounds of the general formula, especially the preferred compounds, are used in combination with the aforementioned insecticides and foliar fungicides.

Other application methods may be used to control the deleterious effects of other nematodes and include spraying above-ground parts such as stems, leaves and buds of plants in which nematodes are already present or where later attack is expected. Examples of these other applications are: dipping or soaking the reproductive parts in an aqueous suspension, solution or emulsion of an active ingredient; dusting above-ground parts or reproductive parts with a dust composition of an active ingredient; or immersing the root system to disinfect the plant or to provide protection against subsequent nematode invasion. The reproductive parts may be seeds, cane pieces, and bulbs which are infested or are to be planted in infested soil.

The effective amount of these compounds, which control nematodes for applying directly to the soil in which nematodes are present, or directly to areas which may become infested with nematodes is from 40 to 500 pounds of a compound per acre, and preferably from 50 to 200 pounds per acre, but generally from 50 to 75 pounds per acre.

For a more effective control of the deleterious effects of root-knot nematodes upon plants, particularly Meloidogyne species, especially *Meloidogyne incognita*, it is preferable to apply a control nematocide such as a stable metal azide, stable metal azide-metal salt formulations of azides, Nemagon, or S-4-methoxyphenyl N-(2,2-dimethyl-2-propynyl)thiolcarbamate, but not those of the general formula wherein the aryl is phenyl, to the soil before planting the crops so as to reduce the number of pathogenic nematodes contained therein, and then after planting the crop to maintain control of the deleterious effects of nematodes on the plants by applying an effective amount of S-4-methoxyphenyl N-(2,2-dimethyl-2-propynyl)thiolcarbamate or other of the preferred compounds disclosed herein, systemic nematode controlling compound to systemically control the deleterious effects of the nematodes.

It is best to remove as much of the pathogenic pests from the soil, by applying azide compounds mentioned herein, or Nemagon, Nemacur, or the thiolcarbamates disclosed herein as well as Nemagon (1,2-dibromo-3-chloropropane), Nemacur (O-phenyl N,N'-dimethylphosphorodiamidate), as well as soil fungicides and insecticides, such as: Captan (cis-N-((trichloromethyl)-thio)-4-cyclohexene-1,2-dicarboximide), Dexon (p-dimethylaminobenzenediazo sodium sulfate), PCNB (pentachloronitrobenzene), Furadan (2,3-dihydro-2,2-dimethyl-7-benzofuranylmethylcarbamate), Mocap (O-ethyl S,S-dipropylphosphorodithioate), or Temik (2-methyl 2(methylthio)propionaldehyde O-(methylcarbamoyl)oxime), prior to planting the crops followed by one or more applications of preferred disclosed compounds such as S-4-methoxyphenyl N-(1,1-dimethyl-2-propynyl)thiolcarbamate to the plant's foliage during plant growth to maintain better systemic control of the deleterious effects of nematodes.

The systemic nematode controlling compounds disclosed herein, i.e., S-4-methoxyphenyl N-(1,1-dimethyl-2-propynyl)thiolcarbamate are effective to control the deleterious effect of nematode particularly Meloidogyne genus and in particular the specie *Meloidogyne incognita* upon plants affected by these nematodes; especially plants such as ornamentals, banana, avocado, sugar cane, pineapple, tobacco, citrus, soybeans, coffee, peanuts, corn, cucumbers, or garden crops such as sweet potato, tomato, carrot, celery, sugar beets, potato, etc.

The following example illustrates a suitable emulsifiable concentrate formulation, for dilution in water for spraying plants, particularly, plant foliage or for application to other plant parts as herein mentioned. Thus, in this emulsifiable concentrate formulation, the percentages are by weight percent.

EXAMPLE LI

| EMULSIFIABLE CONCENTRATE FORMULATIONS | |
|---|---|
| S-4-methoxyphenyl N-(1,1-dimethyl-2-propynyl)thiolcarbamate | 13% |
| Xylene | 41% |
| Isophorone | 41% |
| ATLOX ® 3404* | 1% |
| ATLOX ® 3403 F* | 4% |

*Commerical emulsifier for agricultural pesticides manufactured by Atlas Powder Co., Wilmington, Delaware, and registered with the U.S. Food and Drug Administration.

f. Effective Amount of Compound to Apply to Control the Deleterious Effects of Other Plant Pests The compounds described herein when used for other plant pests, are applied in an amount effective to control the deleterious effects of the plant pests such as fungi, bacteria, and other pathogenic organisms and microorganisms mentioned herein. The plant pests referred to herein and in the claims include those specifically described and shown herein as well as equivalent species which are biologically related and whose deleterious effects may be controlled by contacting plants with the compounds mentioned herein, such as species of the genus Meloidogyne, Fusarium, Sclerotium, and Puccinia.

A single compound may be used in the formulation described herein, preferably a plurality of the compounds are used together either in a formulation or by concurrent application, that is applying one or more compounds to the soil and one or more of the same or different compounds to the plant itself. In other applications, one or more compounds of the general formula may be applied to the soil, or the plant, and within about 10 days, the same compounds, or different compounds of the general formula may be applied to either the soil or the plant so as to effectively control plant pests.

When applied as foliar fungicides, the rate of application is from 20 parts per million (ppm) to the amount tolerated by the plant (up to 50,000 ppm), generally the application rate is from 500 to 1000 parts per million (ppm) of one or more of the active compounds, applied as a solution to the point of run off, or as a powder or dust which thinly coats the plant desired to be covered.

As soil fungicides, the amount is from 0.5 pounds per acre to the maximum tolerated by desirable plants, generally plants, generally from 1.0 pound per acre to 500 pounds per acre, per 6 inch depth of soil, preferably from 20 pounds per acre to 200 pounds per acre per 6 inch depth of soil, but more normally from 20 to 100 pounds per acre per 6 inch depth of soil.

The compounds may be prepared as emulsifiable concentrate formulation, as in Example LI, with the concentration of S-4-methoxyphenyl N-(1,1-dimethyl-2-propynyl)thiolcarbamate or other appropriate thiolcarbamate disclosed herein in the emulsifiable concentrate varying from 5 to 15 weight percent. The xylene may vary from 35 to 45 weight percent, isophorone may vary from 38 to 45 weight percent, ATLOX ®3404 may vary from 0.5 to 3.0 weight percent and ATLOX ®3404 F may vary from 3 to 6 weight percent.

While the invention has been described with reference to specific details of certain illustrative embodiments, it is not intended that it shall be limited thereby except insofar as such details appear in the accompanying claims.

I claim:

1. A composition represented by the general formula:

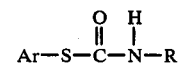

wherein:
Ar is an aryl selected from the group consisting of phenyl, 4-chlorophenyl, 4-bromophenyl, 4-fluorophenyl, 3,4-dichlorophenyl, 4-nitrophenyl, 3-alkoxyphenyl in which the alkoxy has from one to four carbon atoms, 4-alkoxyphenyl in which the alkoxyphenyl has from one to four carbon atoms, 3-alkylphenyl in which the alkyl has from one to four carbon atoms, and 4-alkylphenyl in which the alkyl has from one to four carbon atoms, and R is an alkynyl selected from the group consisting of 2-propynyl, 2-butynyl, 3-butynyl, 2-pentynyl, 3-pentynyl, 4-pentynyl, 1-methylprop-2-ynyl, 1-ethylprop-2-ynyl, 1-methylbut-2-ynyl, and 1,1-dimethylprop-2-ynyl.

2. The composition of claim 1, wherein R is an alkynyl selected from the group consisting of 1,1-dimethylprop-2-ynyl, 2-propynyl, and 1-methylprop-2-ynyl.

3. The composition of claim 1, wherein R is 1,1-dimethylprop-2-ynyl.

4. The composition of claim 1, wherein Ar is an aryl selected from the group consisting of 4-methoxyphenyl, 3-methoxyphenyl, 3,4-dichlorophenyl, 4-chlorophenyl, and phenyl.

5. The composition of claim 4, wherein R is an alkynyl selected from the group consisting of 1,1-dimethylprop-2-ynyl, 2-propynyl, and 1-methylprop-2-ynyl.

6. The composition of claim 4, wherein R is 1,1-dimethylprop-2-ynyl.

7. S-4-methoxyphenyl N-1,1-dimethylprop-2-ynylthiolcarbamate.

8. S-3-methoxyphenyl N-1,1-dimethylprop-2-ynylthiolcarbamate.

9. S-3,4-dichlorophenyl N-1,1-dimethylprop-2-ynylthiolcarbamate.

10. S-4-chlorophenyl N-1,1-dimethylprop-2-ynylthiolcarbamate.

11. S-phenyl N-1,1-dimethylprop-2-ynylthiolcarbamate.

12. A method of controlling the deleterious effects of a nematode of the genus Meloidogyne which comprises:
    contacting a plant with S-4-methoxyphenyl N-1,1-dimethylprop-2-ynylthiolcarbamate in an amount effective to control the deleterious effect upon the plant of a nematode of the genus Meloidogyne.

13. The method of claim 12, wherein the nematode is the species *Meloidogyne incognita.*

14. A method of controlling the deleterious effects of a fungus of the genus Fusarium on plants which comprises:
    contacting a plant with a composition in an amount effective to control the deleterious effects upon the plant of a fungus of the genus Fusarium, said composition represented by the general formula:

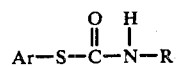

wherein:
Ar is an aryl selected from the group consisting of phenyl, 4-chlorophenyl, 4-bromophenyl, 4-fluorophenyl, 3,4-dichlorophenyl, 4-nitrophenyl, 3-alkoxyphenyl in which the alkoxy has from one to four carbon atoms, 4-alkoxyphenyl in which the alkoxyphenyl has from one to four carbon atoms, 3-alkylphenyl in which the alkyl has from one to four carbon atoms, and 4-alkylphenyl in which the alkyl has from one to four carbon atoms, and
R is 1,1-dimethylprop-2-ynyl.

15. A method of controlling the deleterious effects of a fungus of the genus Sclerotium upon plants which comprises:
    contacting a plant with S-4-methoxyphenyl N-1,1-dimethylprop-2-ynylthiolcarbamate in an amount effective to control the deleterious effects upon the plant of a fungus of the genus Sclerotium.

16. A method of controlling the deleterious effects of a fungus of the genus Puccinia upon plants which comprises:
    contacting a plant with S-4-methoxyphenyl N-1,1-dimethylprop-2-ynylthiolcarbamate in an amount effective to control the deleterious effects upon the plant of a fungus of the genus Puccinia.

17. The method of claim 14, wherein the fungus is the species *Fusarium solani.*

18. the method of claim 15, wherein the fungus is the species Sclerotium rolfsii.

* * * * *

UNITED STATES PATENT AND TRADEMARK OFFICE
CERTIFICATE OF CORRECTION

PATENT NO. : 4,075,006
DATED : February 21, 1978
INVENTOR(S) : Jay K. Rinehart

It is certified that error appears in the above-identified patent and that said Letters Patent are hereby corrected as shown below:

Column 23, line 26, "Meloidogyne" should be italicized after "genus".

Column 23, line 30, "Meloidogyne" should be italicized after "genus".

Column 23, line 34, "Fusarium" should be italicized after "genus".

Column 24, line 1, "Fusarium" should be italicized after "genus".

Column 24, line 20, "Sclerotium" should be italicized after "genus"

Column 24, line 25, Sclerotium should be italicized after "genus".

Column 24, line 27, "Puccinia" was not italicized after "genus".

Column 24, line 32, "Puccinia" should be italicized after "genus".

Column 24, line 36, Sclerotium rolfsii" should be italicized after "species"

Signed and Sealed this

Third Day of October 1978

[SEAL]

Attest:

RUTH C. MASON
Attesting Officer

DONALD W. BANNER
Commissioner of Patents and Trademarks